United States Patent [19]

Sperber et al.

[11] Patent Number: 5,023,337
[45] Date of Patent: Jun. 11, 1991

[54] CHEMICAL PROCESS FOR THE PREPARATION OF PHARMACEUTICALLY ACTIVE COMPOUNDS

[75] Inventors: Ferenc Sperber; Csaba Huszar, both of Budapest; Attila Németh, Göd; Éva Somfai; Irén Páli nee Ivanics, both of Budapest, all of Hungary

[73] Assignee: Chinoin Gyogyszer- Es Vegyeszeti Termekek Gyara Rt., Budapest, Hungary

[21] Appl. No.: 469,749

[22] Filed: Jan. 19, 1990

Related U.S. Application Data

[63] Continuation of Ser. No. 226,411, Jul. 29, 1988, abandoned.

[30] Foreign Application Priority Data

Jul. 30, 1987 [HU] Hungary ............................... 3510/87

[51] Int. Cl.$^5$ ............................................ C07D 235/30
[52] U.S. Cl. ..................................... 548/306; 548/329
[58] Field of Search ................................ 548/306, 329

[56] References Cited

U.S. PATENT DOCUMENTS

3,325,470  6/1967  Ribka ................................ 534/866

OTHER PUBLICATIONS

*Chemical Abstracts*, 100: 174242 d (1984) [Valitov, F., Deposited Doc. 1982, Viniti 6343-82, 103-11].
*Chemical Abstracts*, 97:38617x (1982) [Alberola, A., et al., *An. Quim. Ser. C.* 1982, 78(1), 67-72].
*Chemical Abstracts*, 102:6257k(1985) [Alberola, A., et al., *An. Quim. Ser. C*, 1984, 80(1), 59-64].
Fiester, L. et al., *Reagents for Organic Chemistry*, John Wiley, New York, 1967, pp. 1179-1181.
March, J., *Advance Organic Chemistry*, McGraw Hill, New York, 1968, pp. 319-320 and 335.
Alberola, A., et al., Alkylaluminums, XXVII. Reaction of Carboxylic Acid Chlorides with Triphenylaluminum, *An. Quim, Ser. C* 1982, 78(1), pp. 67-72.
Alberola, A. et al., Behavior of 4–Alpha–Haloalkylisoxazoles Toward Organomagnesium and Organoaluminum Compounds, *An. Quim. Ser. C*, 1984, 80(1), pp. 59-64.
Valitov, F. H., Synthesis of Ketones from Aluminiumorganic Compounds and Chlorohydrides of Acids. U.S.S.R., Deposited Document 1982. This is the underlying reference in Chem. Abstracts 100:174242d (1984) cited by the Examiner as Chem Abstracts (®).

*Primary Examiner*—Mary C. Lee
*Assistant Examiner*—Lenora A. Miltenberger
*Attorney, Agent, or Firm*—Herbert Dubno; Jonathan Myers

[57] ABSTRACT

The present invention is directed to the preparation of benzimidazole derivatives of the formula (I),

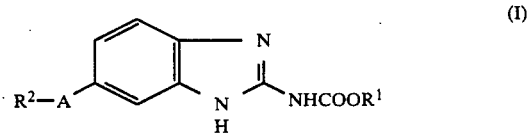

(I)

wherein
 A = stands for S, SO or SO$_2$,
 R$^1$ = stands for C$_{1-4}$ alkyl group,
 R$^2$ = stands for C$_{1-4}$ alkyl, C$_{3-7}$ cycloalkyl or C$_{6-10}$ aryl or aralkyl,
comprising reacting a sulphochloride of the formula (II)

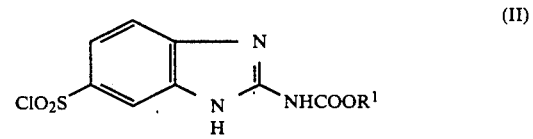

(II)

with an alkyl aluminum compound of the formula (III).

R$_n^2$AlClhd (3-n)   (III)

The reaction is performed in one step.

2 Claims, No Drawings

CHEMICAL PROCESS FOR THE PREPARATION OF PHARMACEUTICALLY ACTIVE COMPOUNDS

This is a continuation of co-pending application Ser. No. 07/226,411 filed on 29 Jul. 1988, now abandoned.

FIELD OF THE INVENTION

The present invention is related to a process for the preparation of pharmaceutically active compounds.

BACKGROUND OF THE INVENTION

It is known that 5(6)-substituted benzimidazole-2-carbamate derivatives of the formula (I)

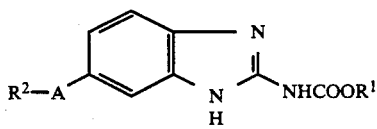

can be used in therapy due to their anthelmintic effect.

In the following formulae the definition of the substituents is as follows:

A stands for S, SO or $SO_2$,
$R^1$ stands for a $C_{1-4}$ alkyl group,
$R^2$ stands for $C_{1-4}$ alkyl, $C_{3-7}$ cycloalkyl or $C_{6-10}$ aryl or aralkyl,
n stands for 1, 2 or 3.

In order to indicate the position of the 5(6) substituent we may hereinafter refer to a 5-substituent, but we do not wish thereby to fix the position.

The compounds and their synthesis are described in the following patents: GB Nos. 1,123,317, 1,464,326, 1,455,728, DE No. 2,438,120, BE No. 817,364 and U.S. Pat. Nos. 3,738,993 and 4,076,827.

For the preparation of 5(6)-alkyl-sulfenyl-derivatives of the formula (IV)

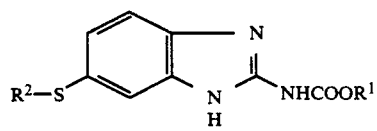

a process is further disclosed in Hungarian patents Nos. 182,763 and 182,782 and in Hungarian patent application No. 4725/84.

The common feature of the processes directed to the preparation of the above compounds is that the sulfinyl group is obtained by using various oxidizing agents such as hydrogen peroxide, peracetic acid, m-chloro-perbenzoic acid from a suitable sulfenyl and the difference is only whether the already prepared alkyl-sulfenyl-benzimidazole is oxidized or the starting 1,2-N-substituted alkyl-sulfenyl-benzene is oxidized which is suitable for the preparation of the latter compound.

According to the above mentioned patents the formation of the 5-alkyl-sulfenyl-group can be performed essentially by the following three methods:

1. 1,2-N-substituted-4-halogen-benzene or 5-halogen-benzimidazole-2-carbamate is reacted with alkali-mercaptide or sodium-hydrogene-sulfide followed by reaction with alkyl or aryl-halide.

2. Thio-cyanic-acid-ester is obtained from 1,2-N-substituted-4-halogen-benzene or 5(6)-halogen-benzimidazole-2-carbamate with alkali-rhodanide and the thio-cyanic-acid-ester is further reacted with alkyl or aryl-halide to produce a thio-ether (HU No. 182,763).

3. The 1,2-N-substituted benzene or benzimidazole-2-carbamate is sulfo-chlorinated at the 5(6)-position and the obtained sulfo-chloride is reduced to mercaptan or disulfide and the thio-ether is prepared from the obtained mercaptan or disulfide by reaction with alkyl or aryl halide (HU No. 182,782 or Hungarian patent application No. 4725/84).

The common feature of the mentioned reaction methods is the formation of the molecule in several steps and the yield of the individual steps is much lower than required to be economical and due to the various possibilities of side-reactions no homogeneous product is obtained.

The sulphinyl derivatives of the formula (V)

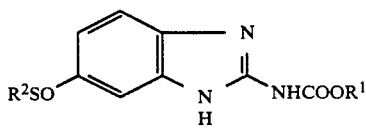

can be prepared by the known oxidation of the 5-alkyl-sulphenyl derivative (HU No. 169,272).

DESCRIPTION OF THE INVENTION

According to the present invention the desired molecule can be formed by a new approach based on according to which the reduction of the sulphur atom and the alkylation can be performed in one step by using one reactant.

The present invention is directed to the preparation of benzimidazole derivatives of the formula (I) by reacting a sulpho-chloride of the formula (II)

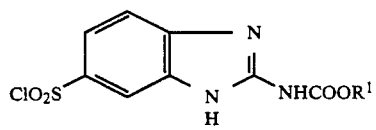

with an alkyl aluminum compound of formula (III).

Our process of the present invention can be used for the preparation of the derivatives substituted by $R^2$-sulphenyl, $R^2$-sulphinyl and $R^2$-sulphonyl groups.

It depends on the reaction conditions which product is produced among the desired derivatives and the determination of the products is also provided by the present invention.

In order to prepare a group of the compounds of the formula (I) i.e. the 5-$R^2$-sulphenyl derivatives of the formula (IV) a sulphochloride of the formula (II) is reacted with at least 3, preferably 3 to 3.5 moles of aluminum-alkyl of the formula (III) for 0.5–3 hours at 20°–100° C.

In order to prepare another group of the compounds of the formula (I) i.e. the sulfinyl derivatives of the formula (V)

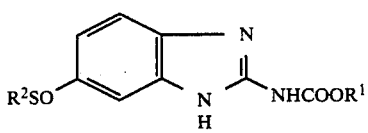

a compound of the formula (II) is reacted with aluminum-alkyl of the formula (III) at a molar ratio of 1:2 at atmospheric pressure at a temperature of 20° to 100° C.

In order to prepare another group of the compounds of the formula (I) i.e. the sulphonyl derivatives of the formula (VI)

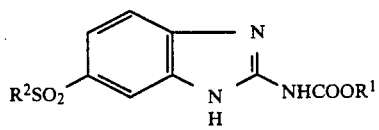

1 mole of the sulpho-chloride of the formula (II) is reacted with the aluminum compound of the formula (III) at 2-2.5 bar and at 20°-100° C. For this reaction preferably an aluminum-alkyl of the formula $R^2AlCl_2$ is used as the compound of the formula (III).

The compounds of the formulae (II) and (III) are reacted preferably in the presence of a solvent under a nitrogen atmosphere. As a solvent preferably dichloro methane, chloroform, carbon tetrachloride, hexane or glacial acetic acid and/or light benzin-fractions are used.

The starting materials are known. The compounds of the formula (II) can be prepared e.g. according to HU No. 182,782 and various alkyl aluminum compounds are commercial products.

The details of the process of the invention are further illustrated in the following non-limiting examples.

EXAMPLE 1

2.9 g of 5-chlorosulphonyl-2-carbomethoxyamino-benzimidazole are suspended in 10 ml of dichloromethane, 1.4 g of propyl-aluminum-dichloride are added, the mixture is poured into a bomb pipe flushed with nitrogen, sealed and placed into a water bath of a temperature of 70° C. It is kept in this bath for 0.5 hour. The ampoule is opened and its content is poured into a distillation flask and the solvent is distilled off. 20 ml of water are added to the residue and the pH is adjusted to acidic by adding diluted sulphuric acid, the obtained suspension is filtered, the residue is washed and dried. The obtained crude product is recrystallized from glacial acetic acid. 2.67 g 5-m-propyl-sulphonyl-2-carbomethoxy-amino-benzimidazole are obtained.
Mp.: 280° C.

EXAMPLE 2

2.9 g of 5-chlorosulphonyl-2-carbomethoxyamino-benzimidazole are suspended in 10 ml dichloromethane and 3.2 g aluminum-tri-n-propyl are added. The reaction mixture is boiled under cooling in a nitrogen atmosphere for 30 minutes, whereafter 20 ml of water are added and it is acidified to pH 1 by adding diluted sulphuric acid. The aqueous layer is separated and neutralized by adding a 30% sodium hydroxide solution. The obtained suspension is filtered and the residual substance is washed with water and covered with acetone and dried. The crude product is recrystallized from glacial acetic acid. 2.3 g of 5(6)-n-propyl-sulphinyl-2-carbomethoxy-benzimidazole are obtained.
Mp.: 191° C.

EXAMPLE 3

2.9 g of 5-chlorosulphonyl-2-carbomethoxyamino-benzimidazole are suspended in 10 ml of n-hexane and 4.5 g of n-propyl-aluminum-di-chloride are added. The reaction mixture is heated under reflux for 3 hours in nitrogen atmosphere. 30 ml of water are added and the pH is adjusted to 1 by adding diluted sulphuric acid, the aqueous layer is separated. The pH of the solution is adjusted to neutral by adding a 30% sodium hydroxide solution, the obtained suspension is filtered and the residue is washed with water, covered with acetone and dried. The crude product is recrystallized from glacial acetic acid. 2.15 g of 5(6)-n-propyl-sulphenyl-2-carbomethoxy-amino-benzimidazole are obtained.
Mp.: 213° C.

EXAMPLE 4

One may proceed according to example 2 but 2.9 g of 5-chlorosulphonyl-2-carbomethoxyimino-benzimidazole are suspended in 10 ml benzin and 3.5 g of phenyl-aluminum-dichloride are added dropwise, admixed with 10 ml of benzin. The reaction proceeds at 100° C. for 1 hour in a nitrogen atmosphere and the reaction mixture is worked up in order to get 1.6 g of 5(6)-phenyl-sulphinyl-2-carbomethoxy-amino-benzimidazole.
Mp.: 254° C. (dec.).

EXAMPLE 5

One proceeds according to example 2 but to the solution of 2.9 g 5-chlorosulphonyl-2-carbomethoxy-amino-benzimidazole in 20 ml chloroform 1.3 g of ethyl-aluminum-dichloride are added, whereafter the reaction mixture is heated in a nitrogen atmosphere for 30 minutes and a solution of 2.35 g dicyclohexyl-aluminum-chloride and 10 ml n-hexane is added dropwise and the mixture is boiled under reflux for 1 hour. After working up the reaction mixture 1.98 g 5(6)-cyclohexyl-sulphinyl-carbomethoxy-amino-benzimidazole are obtained.
Mp.: 191° C.

THE PREPARATION OF THE STARTING MATERIAL

To 200 g of chlorosulphonic acid 25 g of methyl-benzimidazolyl-2-carbamate are added. The reaction mixture is maintained at this temperature for 3 hours, poured on 500 g of ice and the obtained suspension is stirred for 5 minutes, filtered and washed with ice water. The product is dried in air. 27 g of 5-chlorosulphonyl-2-carbomethoxy-amino-benzimidazole are obtained.

We claim:
1. A process for the preparation of a compound of the Formula (I)

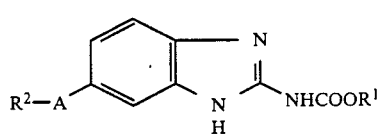

wherein
A is S, SO or $SO_2$;
$R^1$ is $C_1$ to $C_4$ alkyl; and $R^2$ is $C_1$ to $C_4$ alkyl, which comprises reacting a compound of the Formula (II)

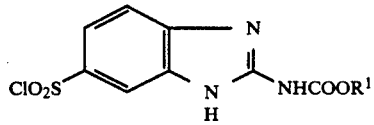

at 20° to 100° C. in an organic solvent with a compound of the Formula (III)

$R^2{}_n AlCl_{(3-n)}$ wherein n is 1, 2 or 3, whereby
 (a) for producing the compound of the Formula (I) where A is S, the molar ratio of the compound of the Formula (II) to the compound of the Formula (III) is 1:3 to 3.5;
 (b) for producing the compound of the Formula (I) where A is SO, the molar ratio of the compound of the Formula (II) to the compound of the Formula (III) is 1:2; and
 (c) for producing the compound of the Formula (I) where A is $SO_2$, the molar ratio of the compound of the Formula (II) to the compound of the Formula (III) is 1:1.

2. A process according to claim 1 which comprises using as the organic solvent dichloro-methane, chloroform, carbon-tetrachloride, hexane, glacial acetic acid or a light benzin-fraction.

* * * * *